US008155735B2

(12) United States Patent
Bashour et al.

(10) Patent No.: US 8,155,735 B2
(45) Date of Patent: Apr. 10, 2012

(54) PREDICTION AND PREVENTION OF POSTOPERATIVE ATRIAL FIBRILLATION IN CARDIAC SURGERY PATIENTS

(75) Inventors: C. Allen Bashour, Chagrin Falls, OH (US); Bala Gopakumaran Nair, Bellevue, WA (US); Mirela Visinescu, Fairview Park, OH (US); Meng Xu, Lyndhurst, OH (US); Liang Li, Solon, OH (US); Mohamed H. Bakri, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 1152 days.

(21) Appl. No.: 11/855,207

(22) Filed: Sep. 14, 2007

(65) Prior Publication Data

US 2008/0167567 A1 Jul. 10, 2008

Related U.S. Application Data

(60) Provisional application No. 60/845,726, filed on Sep. 19, 2006.

(51) Int. Cl.
*A61B 5/0402* (2006.01)

(52) U.S. Cl. ............. 600/518; 600/509; 600/515; 607/9

(58) Field of Classification Search .................. 600/508, 600/510, 515, 516, 518; 607/9
See application file for complete search history.

(56) References Cited

U.S. PATENT DOCUMENTS

| | | | | |
|---|---|---|---|---|
| 4,589,420 | A | 5/1986 | Adams et al. | |
| 5,092,343 | A | 3/1992 | Spitzer et al. | |
| 5,280,792 | A | 1/1994 | Leong et al. | |
| 5,456,261 | A | 10/1995 | Luczyk | |
| 5,819,007 | A | 10/1998 | Elghazzawi | |
| 6,192,273 | B1 | 2/2001 | Igel et al. | |
| 7,025,729 | B2 | 4/2006 | de Chazal et al. | |
| 7,058,444 | B2 | 6/2006 | Logan et al. | |
| 2004/0092836 | A1* | 5/2004 | Ritscher et al. | 600/518 |
| 2005/0222508 | A1 | 10/2005 | Moreno et al. | |
| 2005/0224086 | A1* | 10/2005 | Nahon | 128/899 |
| 2006/0136414 | A1* | 6/2006 | Roach et al. | 707/6 |

OTHER PUBLICATIONS

Visinescu et al., "Automatic Detection of Conducted Premature Atrial Contractions to Predict Atrial Fibrillation in Patients after Cardiac Surgery", *Computers in Cardiology*, 2004; 31:429-432.

Visinescu et al., "Automatic Detection of QRS Complexes in ECG Signals Collected from Patients After Cardiac Surgery", *Engineering in Medicine and Biology Society, 2006, EMBS '06, 28th Annual International Conference of the IEEE*, Aug. 2006, pp. 3724-3727.

* cited by examiner

*Primary Examiner* — Carl H Layno
*Assistant Examiner* — Pamela M Bays
(74) *Attorney, Agent, or Firm* — Tarolli, Sundheim, Covell & Tummino LLP

(57) ABSTRACT

Systems and methods are provided for predicting the onset of postoperative atrial fibrillation (AF) from electrocardiogram (ECG) data representing a patient. A signal processing component determines parameters representing the activity of the heart of the patient from the ECG data. A feature extraction component calculates a plurality of features useful in predicting postoperative AF from the determined parameters. A classification component determines an AF index for the patient from the calculated plurality of features. The AF index represents the likelihood that the patient will experience AF.

8 Claims, 6 Drawing Sheets

PREDICTION AND PREVENTION OF POSTOPERATIVE ATRIAL FIBRILLATION IN CARDIAC SURGERY PATIENTS

RELATED APPLICATION

This application claims priority from U.S. Provisional Patent Application Ser. No. 60/845,726, filed Sep. 19, 2006, the subject matter of which is incorporated herein by reference.

FIELD OF THE INVENTION

The present invention relates to a system and method for predicting outcomes of clinical procedures and, in particular, is directed to systems and methods for non-invasively predicting the first onset of postoperative atrial fibrillation in cardiac surgery patients.

BACKGROUND OF THE INVENTION

Atrial fibrillation (AF) occurs in up to approximately thirty-five percent of patients in the postoperative period after cardiac surgery. This postoperative complication is associated with increased hospital costs, which average as much as $8000 per patient, as well as increased morbidity and mortality. Postoperative atrial fibrillation (pAF) increases the length of a patient's stay in an intensive care unit and a hospital generally, and can result in a low cardiac output state and hemodynamic instability, blood clot formation in the heart (i.e., atria) that can embolize to the lungs to cause pulmonary embolus, to the brain, resulting in stroke, and to other end organs, such as the kidneys, causing acute renal failure, the intestines, causing mesenteric ischemia, and the limbs, potentially resulting in the loss of the limb.

The treatment of pAF depends on the associated clinical findings. If the patient is hemodynamically unstable, they undergo urgent direct current cardioversion (DCCV). If the patient is stable, the goals of treatment are either heart rate control via a pharmacologic agent or rhythm control via elective DCCV. Each of these treatments requires either antiarrhythmic medication administration (e.g., amiodarone, procainamide) or DCCV, which requires one or both of airway management and procedural sedation. If the patient remains in AF, they will require long term anticoagulation therapy that increases the risk of bleeding, for example, in the brain or gastrointestinal tract and requires continued monitoring. AF is poorly understood and the cause is not known. There are presently no known methods to prevent it or to predict it.

SUMMARY OF THE INVENTION

In accordance with an aspect of the present invention, a system is provided for predicting the onset of postoperative atrial fibrillation (AF) from electrocardiogram (ECG) data representing a patient. A signal processing component determines parameters representing the activity of the heart of the patient from the ECG data. A feature extraction component calculates a plurality of features useful in predicting postoperative AF from the determined parameters. A classification component determines an AF index for the patient from the calculated plurality of features. The AF probability index represents the likelihood that the patient will experience AF.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION OF THE INVENTION

In accordance with an aspect of the present invention, computer based algorithms have been developed to collect and segment electrocardiogram (ECG) data and to identify and characterize premature atrial contraction (PAC) activity, heart rate variability (HRV), and P-wave morphology characteristics that can reliably distinguish patients likely to experience postoperative atrial fibrillation from patients less likely to experience postoperative atrial fibrillation. By identifying characteristic features of patients likely to experience postoperative atrial fibrillation, for example, a mean PAC activity of 0.21 PACs/minute, it is possible to reliably predict the onset of postoperative atrial fibrillation using appropriate statistical analysis techniques and classification models.

Figure 1:
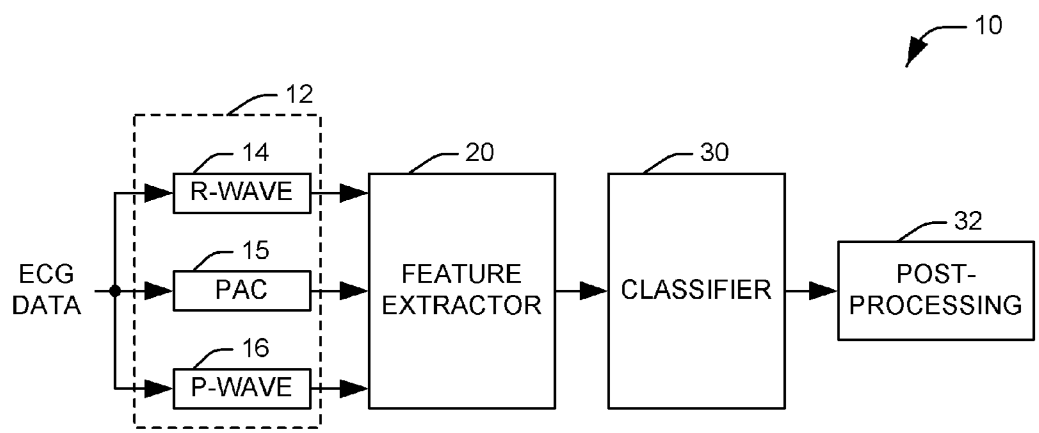
FIG. 1 illustrates a functional block diagram of a system for predicting postoperative atrial fibrillation in accordance with an aspect of the present invention.

FIG. 1 illustrates a functional block diagram of a system 10 for predicting postoperative atrial fibrillation in accordance with an aspect of the present invention. The system 10 identifies and measures electrocardiogram (ECG) characteristics with superior accuracy relative to previous methods and uses the measured ECG characteristics to predict postoperative atrial fibrillation. To this end, ECG data is provided to a signal processing component 12. The signal processing component 12 can comprise a plurality of individual processing components 14-16 that analyze the ECG data to generate medically relevant information from the data. In the illustrated example, the signal processing component comprises three components, an R-wave detector 14, a PAC detector 15, and a P-wave detector 16. It will be appreciated that the individual processing components 14-16 can be interrelated, such that data from a given processing component (e.g., 14) can be provided as input to other components (e.g., 15).

Figure 2:
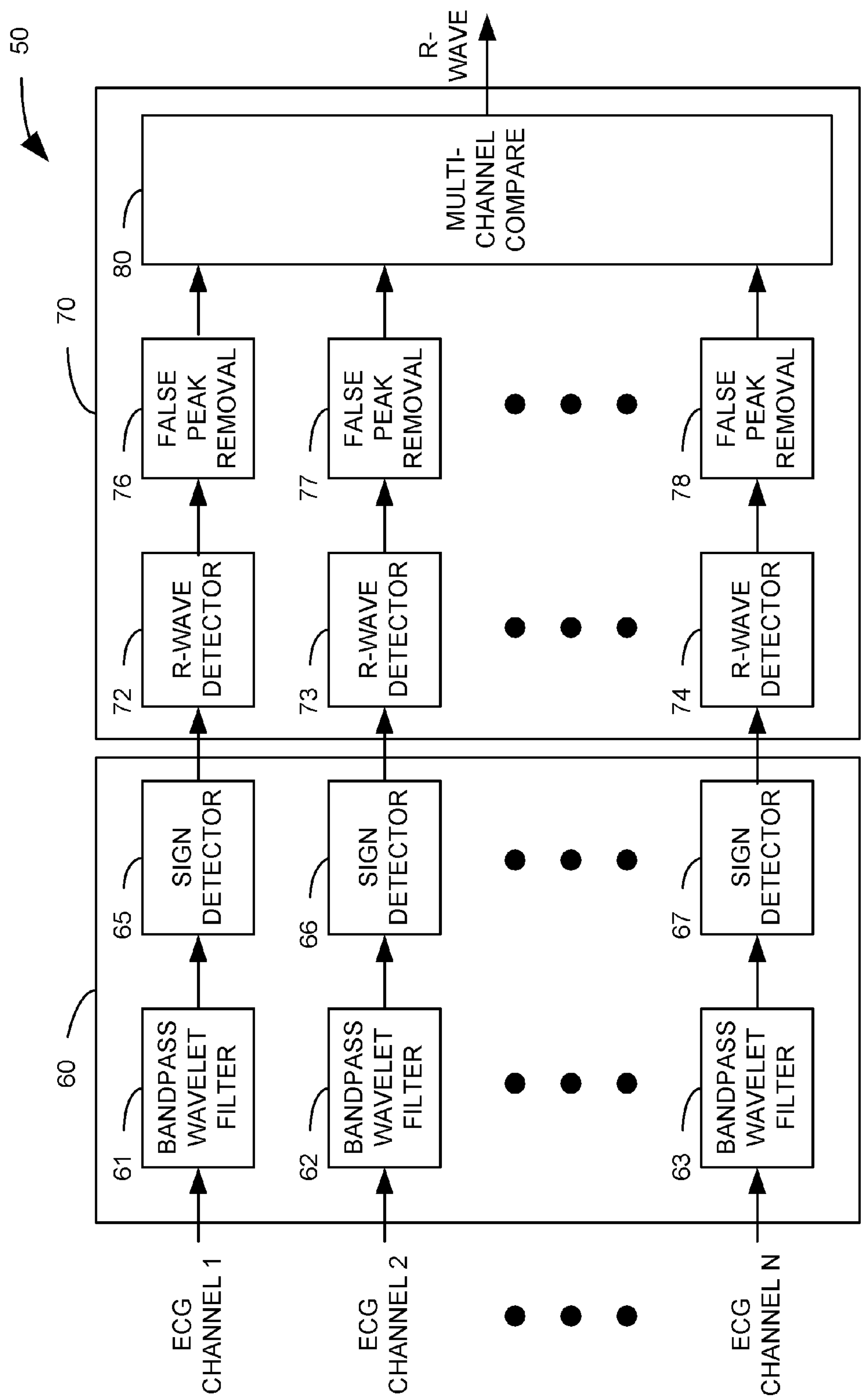
FIG. 2 illustrates a functional block diagram of an exemplary implementation of an R-wave detector system in accordance with an aspect of the present invention.

The R-wave detector 14 is configured to identify R-waves within the ECG data. R-wave detection is the basic and initial step in ECG analysis. R-wave annotation can be used not only for measuring heart rate variability (HRV) parameters, but also for the detection of PACs and P-wave morphology. FIG. 2 illustrates a functional block diagram of an exemplary implementation of an R-wave detector system 50 in accordance with an aspect of the present invention. The illustrated system 50 receives input from a plurality of ECG channels and reviews the input to determine the location of R-waves within the ECG signal.

The R-wave detector system 50 includes a preprocessing stage 60 that mitigates noise within an ECG signal. The preprocessing stage 60 comprises a plurality of denoising prefilters 61-63 that utilize wavelet principles to remove noise and minimize false identification of R-waves within respective channels of the ECG signal. It will be appreciated that the wavelet based prefilters 61-63 are able to, through use of wavelet analysis, provide superior noise removal from the ECG channels compared to existing filtering solutions. Sign detectors 65-67 detect an associated sign of the R-waves, such that the general orientation of the wave is known.

The preprocessed signals from the plurality of channels are provided to a decision making stage 70. The decision making stage 70 identifies and characterizes R-waves within each signal channel. R-waves are identified within each channel at respective R-wave detectors 72-74. In one implementation, the R-wave detectors 72-74 differentiate their respective ECG channels to amplify the R-waves within the channel, facilitating identification of the R-waves. False peaks within each channel are identified and eliminated at respective false peak detectors 76-78. The identified peaks are then provided to a multichannel comparison component 80 that confirms that each R-wave is located in a threshold number of channels (e.g., two) to minimize the effect of artifacts. As a result, the described system 50 is able to detect R-waves with high accuracy (99%) and specificity (99%). The system is able to detect R-waves even in a noisy ECG signal, often outclassing a standard MIT-BIH Physionet algorithm.

Figure 3:
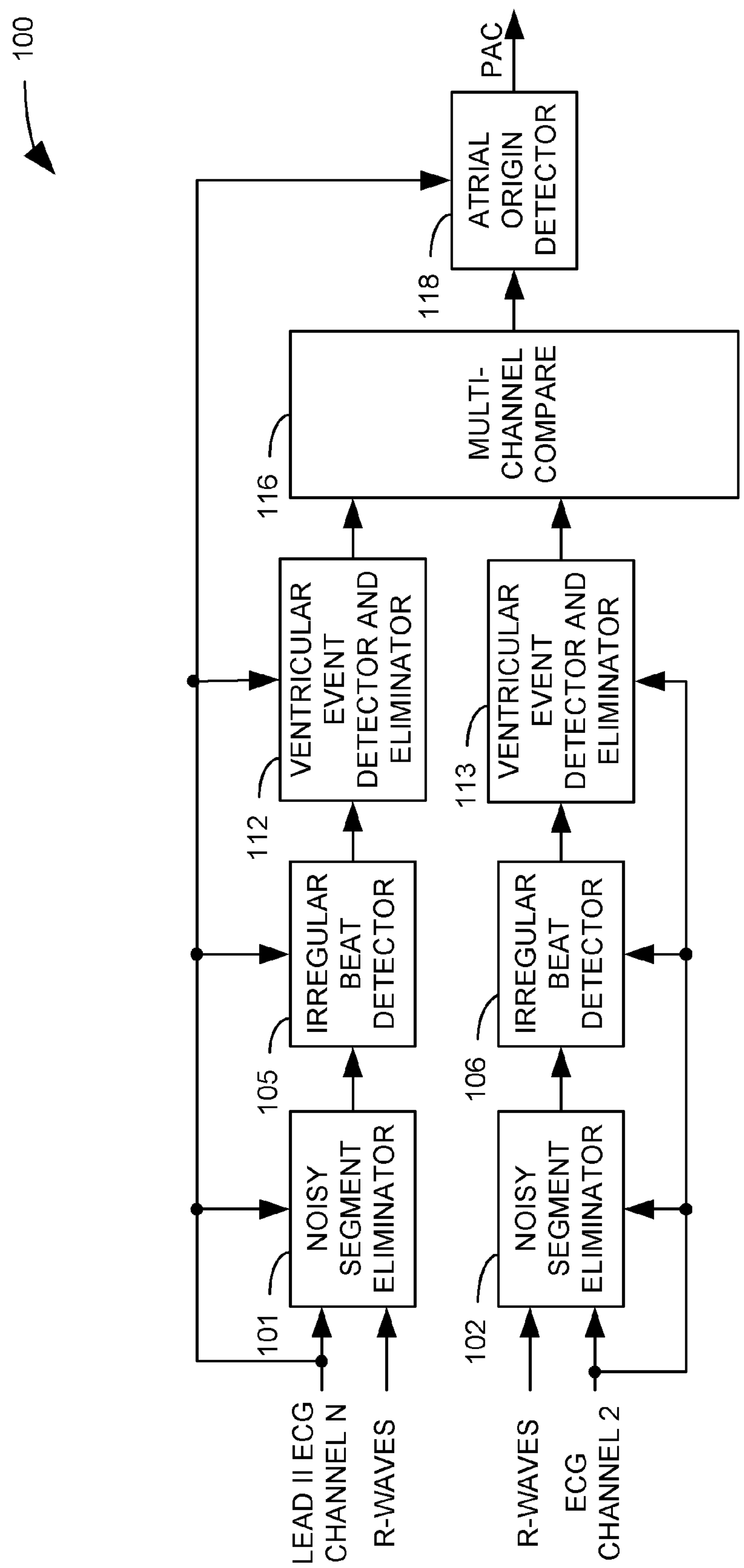
FIG. 3 illustrates a functional block diagram of an exemplary implementation of a PAC detector system in accordance with an aspect of the present invention.

The PAC detector 15 identifies premature atrial contractions represented by the ECG data. FIG. 3 illustrates a functional block diagram of an exemplary implementation of a PAC detector system 100 in accordance with an aspect of the present invention. The illustrated system 100 receives input from a plurality of ECG channels as well as a determined set of R-wave data from an associated R-wave detector system and reviews the input to determine the timing of PACs represented by the ECG signal. In the illustrated system 100, two channels are illustrated, but it will be appreciated that additional channels can be utilized in PAC detection. The ECG inputs for the plurality of ECG channels, along with the detected R-wave data, are provided to respective noisy segment eliminators 101-103, where noise segments within the channel are identified and removed using a first adaptive thresholding algorithm. The denoised channels are then provided to respective irregular beat detectors 105-107 that identify irregular beats within their respective ECG channel via a second adaptive thresholding algorithm. By adaptively varying the threshold values in the first and second thresholding algorithms, the algorithms can accommodate ECG signals that vary in characteristics over time.

The ECG channels are then provided to respective ventricular event evaluators 112-114. Each ventricular event evaluator 112-114 distinguishes between premature atrial beats and premature ventricular beats to allow the system 100 to correctly classify irregular beats. Moreover, to confirm that the irregular beat is a conducted PAC, the presence of P-wave prior to the irregular beat is also detected. An inter-channel comparator 116 confirms PAC occurrences by ensuring that a given PAC is detected in a threshold number of channels (e.g., two) to minimize the effect of artifacts. The determined PACs are then provided to an atrial origin detector 118 that further ensures that each detected event represents a premature atrial contraction. Accordingly, the algorithm is able to detect PACs with high accuracy (97%) and specificity (98%). Many of the previous algorithms to detect PACs were either manual or semi-manual requiring some user intervention. As a significant improvement, the illustrated system 100 is able to detect PACs automatically in real-time. However, a limitation of the system 100 as illustrated is its inability to accurately detect PAC at high (e.g., greater than 120 beats/min) heart rates. This is primarily a result of low tolerance of R-wave thresholds at high heart rates. It will be appreciated, however, that at high heart rates or if a patient is being paced, it is difficult to even manually identify PACs. For most cardiac patients, the heart rate usually remains below this level and they are not paced. The P-wave detector 16 provides automated detection of P-waves represented by the ECG data.

Figure 4:
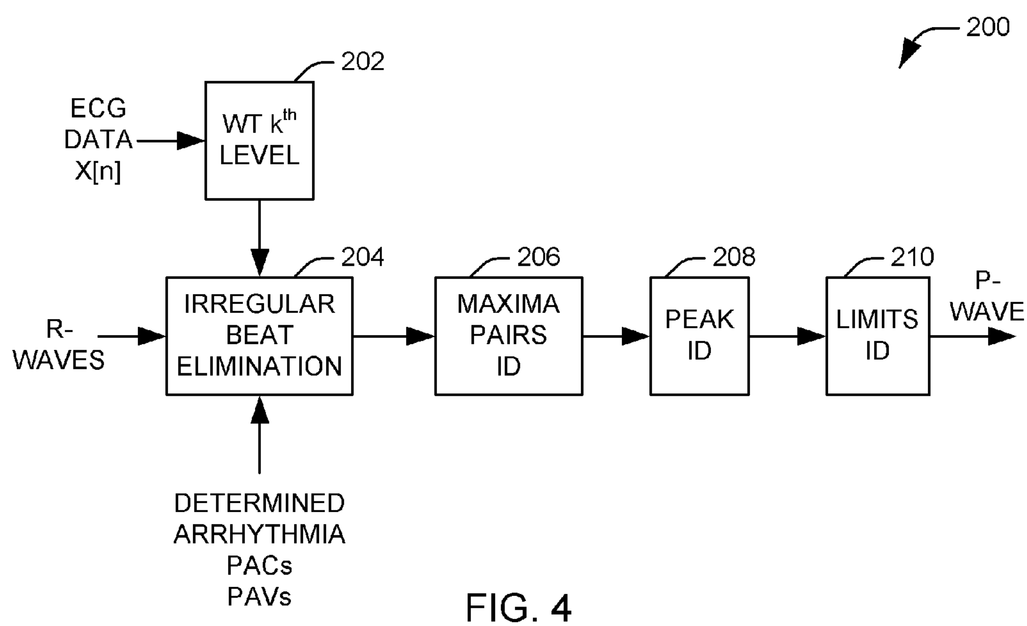
FIG. 4 illustrates a functional block diagram of an exemplary system that utilizes wavelet analysis to automatically detect P-waves in accordance with an aspect of the present invention.

FIG. 4 illustrates a functional block diagram of an exemplary system 200 that utilizes wavelet analysis to automatically detect P-waves in accordance with an aspect of the present invention. Using wavelet methods, it is possible to accurately separate small amplitude P-waves from a non-stationary ECG signal. A wavelet transform (WT) component 202 receives ECG signal data (x[n]) and uses a wavelet function that is the first derivative of the Gauss function to determine a wavelet transform of the ECG signal. The wavelet transform component then selects a scale ($W_2^4x[n]$) that contains the maximum P-wave energy. An irregular beat eliminator 204 identifies and removes any irregular beats (e.g., premature atrial and/or ventricular beats) and arrhythmic segments of ECG from analysis. A selected segment of the WT signal in the selected scale prior to an identified QRS wave is provided to a maxima pairs identifier 206, where the presence of two maxima points is verified to confirm the presence of a P-wave. A peak identifier 208 uses a threshold algorithm applied to the selected scale is used to locate the P-wave peak. A limit identifier 210 uses a threshold algorithm applied to the selected scale to detect the starting and ending points of the P-wave. The illustrated system 200 is able to extract P-waves with a high degree of accuracy, and the measured P-wave morphology parameters (e.g., P-wave width and height) from the system are consistent with values reported in literature within the field. The illustrated system 200 provides a consistent and accurate means to analyze P-waves, representing a significant improvement over previous, manual identification techniques.

Once the signals have been analyzed, a feature extractor 20 computes features from the detected R-waves, premature atrial contractions (PACs), and P-waves that are useful in predicting postoperative atrial fibrillation. These features can include PAC activity, HRV parameters in time, frequency, and non-linear domains and P-wave morphology parameters. For example, a number of features can be based from the determined PAC data. PAC activity is defined as the number of conducted PACs that occur within a specified time. The number of PACs that occur every minute was computed and averaged across a period of data recording to provide one feature. Increased PAC activity could reflect a diseased or damaged atrial substrate that in turn could predispose a patient towards AF. Additionally, it could also indicate increased chances for potential triggers to initiate AF. Comparison of PAC activity data from patients who experience postoperative atrial fibrillation (AF patients) and patients who do not experience postoperative atrial fibrillation (non-AF patients) has indicated that the two groups of patients do exhibit differences in PAC activity.

Similarly, heart rate variability (HRV) parameters can be measured in time, frequency, and non-linear domains. Measurement of these parameters can be based on standards established by the European Society of Cardiology and the North American Society of Pacing and Electrophysiology.

The determined spacing between R-waves, referred to as the RR-interval signal, is analyzed to remove any atrial and ventricular irregular beats as well as any arrhythmic segments. A linear interpolation technique can be applied to remove any signal discontinuities to produce a modified, but continuous, RR-signal, termed the NN-signal. The NN signal is analyzed to compute HRV parameters, for example, across a five minute window of data that was advanced in steps of one minute. In one implementation, the values within each five minute window can be filtered as a weighted averaging process (e.g., finite impulse response filtering). In the time domain, short-term HRV parameters can be computed, such as the mean NN interval, the standard deviation of the NN interval, and the square root of the mean of the sum of the squares of differences between adjacent NN intervals.

Frequency domain measures of HRV can also be computed as they can often differentiate parasympathetic and sympathetic influences better than time domain parameters. The frequency domain parameters can be computed by Fourier analysis of the NN signal. For example, the frequency domain parameters can include the total power, which is the sum of the magnitude of oscillatory components of the signal, and the high frequency (HF) power, defined as the sum of the magnitude of signal components falling within a frequency band ranging from 0.15 Hz to 0.4 Hz. The high frequency band represents rapid heart rate response that is largely mediated by the parasympathetic nervous system. A low frequency (LF) power, defined as the sum of the magnitude of signal components falling within a frequency band ranging from 0.04 Hz to 0.15 H, represents baroreflex and sympathetic activity. A LF/HF ratio, which is the ratio of the low frequency power to the high frequency power, reflects the balance between the opposing autonomous neural mechanisms. A normalized Low Frequency Power (LFn) can also be calculated, which tends to minimize the effect of changes in the total power on the value of LF component. In clinical trials, the high frequency power feature was found to be especially effective in distinguishing between AF and non-AF patients.

Nonlinear measures of HRV can also be computed as they are frequently able to detect subtle but important changes in interbeat heart rate behavior better than time and frequency domain parameters. The nonlinear measures can include an approximate entropy (ApEN) measure and two heart rate turbulence parameters. The ApEN measure reflects a logarithmic likelihood that sequences of patterns that are temporally close to each other will retain various properties in a next incremental comparison. ApEn is a "regularity statistic" that quantifies the predictability of heart rate fluctuations. A reduced ApEn has been associated with compromised physiology or sickness. The turbulence parameters characterize the short-term oscillations of heart rate after premature beats. It has been determined that the modulation of RR interval sequences after PACs and premature ventricular contractions can provide an indication of later cardiac irregularities. For example, an early acceleration of heart rate after a premature beat has been shown to be related to transient vagal withdrawal. A first parameter, turbulence onset (TO), is defined as the difference between the mean of the first two sinus RR-intervals after a compensatory pause and the last two sinus RR-intervals before an ectopic beat divided by the mean of the last two sinus RR-intervals before the premature beat. A second parameter, turbulence slope (TS) represents the speed of the sinus rhythm deceleration after a premature beat, and can quantified by the steepest regression line between the RR-interval count and duration.

The P-wave of the ECG signal represents the electrical activity of the atria and could indicate the existence of irregularities in electrical conduction. Irregularities could be the result of diseased atrial tissue substrate that may predispose a patient to atrial arrhythmias including AF. Using the detected P-waves, the starting, ending, and maximum points of each P-wave can be determined. Periods of the ECG signal comprising missing or noisy data can be excluded from analysis. In addition, irregular beats that are either ectopic or part of an arrhythmia can also be excluded from the analysis of P-wave features. As with HRV parameters, values for the various P-wave morphology parameters can be calculated as mean values for all P-waves falling within a moving window of five minutes of signal data that is advanced by one minute increments. In one implementation, the values within each five minute window can be filtered as a weighted averaging process (e.g., finite impulse response filtering). The P-wave morphology parameters can include the duration of a P-wave and the amplitude of the P-wave. A P-wave shape parameter can indicate monophasic or biphasic P-waves. A P-wave inflection point parameter can be determined as the duration of the P-wave between the onset and the peak or zero points, and a P-wave energy ratio can be determined as the fraction between a right atrial excitation energy and a total atrial excitation energy.

A classification system 30 calculates an AF index representing the likelihood that a patient will experience postoperative atrial fibrillation from the extracted features. It will be appreciated that the classification system 30 can comprise any appropriate algorithm or system for distinguishing among a plurality of output classes according to one or more features. For example, the classification system 30 can comprise one or an arbitrated combination of statistical classifiers, artificial neural networks, support vector machines, fuzzy reasoners, and self-organizing maps.

In one implementation, the classification system 30 can comprise a statistical classifier trained as part of a multivariable logistic regression model. The multivariable logistic regression model quantifies a relationship between the independent ECG prediction parameters comprising the extracted features and the post surgical outcome (AF or no AF). The logistic regression identifies parameters that show statistically significant differences between the AF and non-AF groups and determines appropriate weighting for each of these parameters. The regression model can be used to calculate an AF index for the patient based the determined weighting for the chosen ECG parameters.

In an exemplary implementation, Receiver Operating Characteristics (ROC) curves can be constructed for interpreting the AF index. A cutoff point can be found from the ROC curve to differentiate between AF and non-AF patients such that an optimal combination of sensitivity and specificity is achieved. It will be appreciated that the prediction accuracy can be verified by applying the model on the testing data set to classify the patients.

In an alternative implementation, the classification system 30 can comprise an artificial neural network (ANN) trained to distinguish between expected post-surgical outcomes according to the extracted features. An artificial neural network is an information paradigm that is inspired by the way biological nervous systems, such as the brain, process information.

Figure 5:
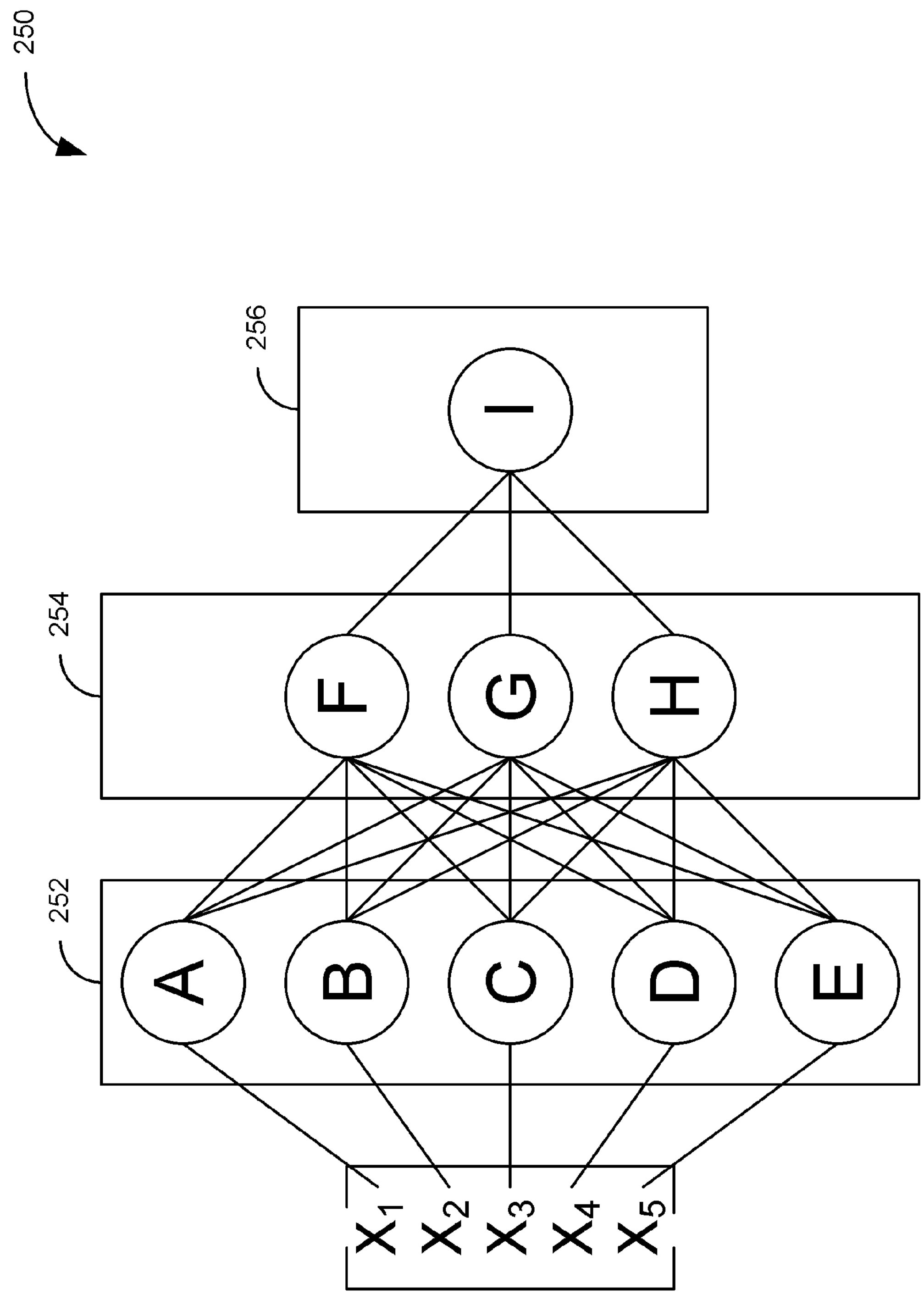
FIG. 5 illustrates an exemplary artificial neural network classifier suitable for use in a postoperative atrial fibrillation classification system in accordance with an aspect of the present invention.

FIG. 5 illustrates an exemplary artificial neural network classifier 250. The illustrated neural network 250 is a three-layer back-propagation neural network suitable for use in a classification system in accordance with an aspect of the present invention. The illustrated architecture, or a similar architecture, can be utilized for simplicity and to minimize overspecialization of the network 250. Depending on the specific implementation, an artificial neural network can utilize more nodes in each layer and/or additional hidden layers. It will be appreciated that a neural network can be implemented in hardware as a series of interconnected hardware processors or emulated as part of a software program running on a data processing system. In the illustrated example, an input layer 252 comprises five input nodes, A-E. A node, or neuron, is a processing unit of a neural network. A node may receive multiple inputs from prior layers which it processes according to an internal formula. The output of this processing may be provided to multiple other nodes in subsequent layers.

Each of the five input nodes A-E receives input signals with values relating to features of an input pattern. Preferably, a large number of input nodes will be used, receiving signal values derived from a variety of pattern features. Each input node sends a signal to each of three intermediate nodes F-H in a hidden layer 254. The value represented by each signal will be based upon the value of the signal received at the input node. It will be appreciated, of course, that in practice, a classification neural network can have a number of hidden layers, depending on the nature of the classification task.

Each connection between nodes of different layers is characterized by an individual weight. These weights are established during the training of the neural network. The value of the signal provided to the hidden layer 254 by the input nodes A-E is derived by multiplying the value of the original input signal at the input node by the weight of the connection between the input node and the intermediate node (e.g., G). Thus, each intermediate node F-H receives a signal from each of the input nodes A-E, but due to the individualized weight of each connection, each intermediate node receives a signal of different value from each input node. For example, assume that the input signal at node A is of a value of 5 and the weights of the connections between node A and nodes F-H are 0.6, 0.2, and 0.4 respectively. The signals passed from node A to the intermediate nodes F-H will have values of 3, 1, and 2.

Each intermediate node F-H sums the weighted input signals it receives. This input sum may include a constant bias input at each node. The sum of the inputs is provided into a transfer function within the node to compute an output. A number of transfer functions can be used within a neural network of this type. By way of example, a threshold function may be used, where the node outputs a constant value when the summed inputs exceed a predetermined threshold. Alternatively, a linear or sigmoidal function may be used, passing the summed input signals or a sigmoidal transform of the value of the input sum to the nodes of the next layer.

Regardless of the transfer function used, the intermediate nodes F-H pass a signal with the computed output value to an output node I in the output layer 256. The weighted output signals from the intermediate nodes are summed to produce an output signal. Again, this sum may include a constant bias input. The value of the output signal produced at the output node is intended to represent the probability that a given input sample belongs to the associated class. The value represented by the output signal can be used as a predictive value for the class.

Training the network involves determining appropriate values for the internode weights such that the error between a desired output and an actual output is minimized for a given input. A training data set, comprising sets of ECG features (e.g., parameters related to PAC activity, HRV and P-wave morphology) that are selected for AF prediction representing a plurality of AF and non-AF patients, can be determined. The outcome, AF or non-AF, can be represented as a numeral, with AF being assigned "100" and non-AF, "0". The training of the ANN can be performed in a supervised manner due to the availability of training data with actual known outcomes. Training is primarily an unconstrained nonlinear minimization problem in which the weights of the network are iteratively modified to minimize the overall mean squared error between the desired and actual output values for all output nodes over all input parameters. This can be accomplished, for example, via a back propagation algorithm. In a back propagation algorithm, the output of the network, when fed with input data, is compared with the true output and the error is propagated backwards through the network altering the weights to reduce the mean-square error. In its basic form, back propagation is a gradient steepest descent method with an associated step size or learning rate that determines the magnitude of weight changes. To improve the speed of convergence, a momentum parameter can be added to make the next weight change in more or less in the same direction as the previous one thus reducing the oscillation effects of larger learning rate. The accuracy of the developed model can be verified by applying the model to predict AF in a testing database. The representative ECG parameter values computed within the moving window will be fed as input to the trained ANN model and the AF prediction index will be determined for each window step. The error between the actual outcome value (100 for AF and 0 for non-AF) and the prediction value can be determined to assess the accuracy of the prediction model.

Another proposed implementation of the classifier 30 is a fuzzy logic classifier that predicts the incidence of postoperative atrial fibrillation based on fuzzy logic rules. Fuzzy logic is based on fuzzy set theory which deals with the concept of partial truth. Thus, in fuzzy set theory, a member can be a partial member of the set. The advantage of fuzzy logic is in its ability to deal with vague, imprecise, noisy, or missing input data as is sometimes the case with atrial fibrillation prediction parameters. Fuzzy logic is capable of reaching a precise conclusion in spite of input data irregularities. This becomes useful in atrial fibrillation prediction because the input parameters could sometimes be missing, be embedded in noise, or fail to satisfy the parameter computation conditions.

To generate a fuzzy logic model, training data representing the ECG prediction variables and the associated outcome for each patient in the training patient group can be determined in a manner similar to that described for neural network model development. To create the fuzzy logic model, the input ECG parameters are "fuzzified" by assigning fuzzy values to each parameter. For example, for the PAC activity parameter, different levels of PAC activity (e.g., high, medium, low) with associated thresholds could be defined as a "fuzzification" step. After fuzzy values or attributes are assigned to each ECG parameter, membership functions can be defined for each attribute. Membership functions define how each point in the input space is mapped to a membership value. The choice of membership functions can be decided during development of the model, and can include any of a number of several standardized membership functions, such as triangular and Gaussian functions.

A set of fuzzy rules can then be articulated, with fuzzy operators defined to combine the outputs of the membership functions. In one example, the fuzzy operators represent a superset of Boolean operators including AND, OR, and NOT. For the atrial fibrillation prediction model, minimum, maximum, and (1−x) fuzzy operators can be used. The fuzzy classifier is then developed, at least in part as a series of IF-THEN fuzzy rules. For simplicity, the fuzzy rules can be initially developed based on heuristics and intuitive knowledge of the relationships between the ECG parameters and the AF outcome. The intuitive knowledge can be gathered by visual analysis of the ECG parameter data by human experts. If this approach is not successful, alternate approaches based on supervised fuzzy clustering to learn the rules from the training data can be adopted. The antecedents of fuzzy rules are the output of the fuzzy operators while the consequent of each rule is a new fuzzy set. Membership functions can be defined for this new fuzzy set as well.

The output fuzzy set that represents all the output of the fuzzy rules can be aggregated in a commutative fashion. A step to "defuzzify" the fuzzy set can be defined to obtain a single numeric output from the fuzzy reasoning process. For example, the defuzzification method can comprise a centroid computation technique. The centroid computation returns the center of the area of the curve defined by the result of aggregation. The numeric output that results from defuzzification process is an AF prediction index, similar to the output of the neural network model. The fuzzy model can be refined iteratively using the training data. If necessary, the membership functions and fuzzy rules can be adjusted in order to obtain the desired relationship between the input features, the ECG parameters, and the output, the AF prediction index.

In one implementation, hybrid systems utilizing fuzzy logic and neural network methods, referred to herein as neuro-fuzzy systems, can be used to calculate the AF index. In a neuro-fuzzy system, much like a standard fuzzy inference system, each of a plurality of "crisp" input values (e.g., non-fuzzy, numerical values) are transformed in a fuzzification step into fuzzy inputs according to their degrees of match with particular categories. For example, a given parameter can be mapped to different discrete categories (e.g., high, medium, low) according to defined thresholds. So, each set of inputs will have different membership strengths based upon the determined categories for the various parameters. The neuro-fuzzy system is effectively defined by a knowledge base, comprising a data base containing functions defining membership strengths for each input and a rule base containing a plurality of if-then fuzzy rules that, in aggregate, provide an output for the system. A firing strength for each rule can be determined from the membership strengths of one or more associated parameters, and when a rule is satisfied by the fuzzy inputs, it provides a qualified consequent based upon the firing strength of the rule. These consequents can be aggregated (e.g., linearly combined, multiplied, etc.) to provide a crisp output for the system.

In general, the development of the knowledge base in fuzzy systems can be based on expert knowledge or experience. Since the knowledge of prediction of AF is very limited, the rules and functions and functions comprising the rule base and the database can not easily be derived from currently available knowledge. Accordingly, to develop the neuro-fuzzy model, a learning process can be utilized in which pairs of input and output data obtained from testing will be presented to the system. The learning process establishes the knowledge base, specifically, the parameters of the membership functions and fuzzy rules, from a plurality of training samples having crisp inputs and outputs.

The establishment of a neuro-fuzzy model involves creating an initial fuzzy rule base from provided data, selecting the significant input variables, finding the optimal number of fuzzy rules, optimizing the parameters in both antecedent and consequent part of the rules, and optimizing the fuzzy system by removing any redundant membership functions. Given N input-output patterns, P(x, y), and a specified error model $\epsilon>0$, creating the initial fuzzy rule base is equivalent to determining a minimal number "k" of fuzzy rules and optimal parameters (c, σ, w) for the fuzzy model F(c, σ, w, k), such that the error function $E=\|y-F\|$ satisfies $E(c, \sigma, w)<\epsilon$, where c is the center of the basis function, σ is the standard deviation or radius, and w are the weight factors. The output of such a fuzzy system is of the form:

$$y = \sum_{i=1}^{k} w_i \prod_{i=1}^{30} \mu_{ij}(x_j) \Big/ \sum_{i=1}^{k} \prod_{j=1}^{30} \mu_{ij}(x_j) \quad \text{Eq. 1}$$

where $\mu_{ij}(x_j)$ is the membership function of input "$x_j$" belonging to the $i^{th}$ fuzzy rule.

In one implementation, the Gaussian function can be used as membership function, such that, $\mu_{ij}(x_j)=\exp\lfloor-(x_j-c_{ij})^2/\sigma_i^2\rfloor$. With this new condition, the output becomes:

$$y = \sum_{i=1}^{k} w_i m_i(x) \Big/ \sum_{i=1}^{k} m_i(x), \quad \text{Eq. 2}$$

where $m_i(x)=\exp\lfloor-\|x-c_i\|^2/\sigma_i^2\rfloor$ represents the matching degree of current input vector "x" to the $i^{th}$ fuzzy rule.

Using the radial basis function (RBF) definition, $$g_i = m_i(x) \Big/ \sum_{i=1}^{k} m_i(x),$$

the relation between input and output can be reduced to:

$$y = \sum_{i=1}^{k} w_i g_i(x). \quad \text{Eq. 3}$$

In an exemplary implementation, an initial fuzzy model, consisting of a collection of fuzzy rules used in AF prediction index, is generated from training data by a self organizing neural network. A fuzzy c-means clustering method is used to determine an optimal number of hidden neurons as well as corresponding receptive fields. Model optimization, including parameter learning and structure simplification, are then performed through a back-propagation learning process to produce a final neuro-fuzzy model.

In the exemplary implementation, a plurality of training samples can be obtained from observation of patient volunteers in a clinical environment. The input parameters for each patient include a set of thirty parameters taken from the P-wave, R-wave, and HRV parameters described previously and their first derivatives. Noise, absence of signal, and artifacts are corrected through transformations and data cleaning methodolgies to limit the data values to physiological ranges. The data values can then be normalized to a unit interval [0,1] to standardize the inputs to the learning network. For a given parameter value, "x", the normalized parameter can be expressed as $$\frac{x-\min}{\max-\min},$$

where "max" and "min" are maximum and minimum values encountered for that parameter.

An AF index, ranging from zero to one-hundred, can be determined for each patient as:

$$AF_{index} = \begin{cases} \frac{100}{(time_{AF\_onset} - 30\text{ min}) - crt\_time}, & \text{when}(time_{AF\_onset} - 30\text{ min}) > \text{crt\_time} \\ 100, & \text{when}(time_{AF\_onset} - 30\text{ min}) \leq \text{crt\_time} \end{cases} \quad \text{Eq. 4}$$

where $time_{AF\_onset}$ is a time of AF onset measured in minutes from the start of ECG registration, and the parameter crt_time is the time measured in minutes from the start of the ECG registration till the current sampling minute.

For patients who do not experience AF, the value of $time_{AF\_onset}=\infty$, so the AF index for these patients will be zero. The thirty minute interval acts as a threshold time after which the AF prediction index is at its maximum value of 100 indicating imminent AF.

Once the data has been gathered, the initial fuzzy model, consisting of a collection of fuzzy rules used in AF prediction index, can be created by a self organizing neural network. Given a set of N data points $\{P_1, P_2 \ldots P_N\}$ that contain the general vector $P_k=(x_{k1}, x_{k2}, \ldots, x_{k30}, y_k)$, with $k=\overline{1,N}$, the self-organizing network can produce a collection of p clusters, $C=(c_1, c_2, \ldots, C_p)$ and p<<N, where "p" is the number of nodes of the competition layer. The center of each cluster from the p clusters can be denoted as $c_i=[x_i^* y_i^*]$ where $x_i^*=(x_{i1}^*, x_{i2}^*, \ldots, x_{i30}^*)$ and $y_i^*=y_i$. Each of these centers is considered as a fuzzy rule that can be described as "IF the input is around $x_i^*$ THEN the output is around $y_i^*$".

Depending on the input vector x*, the degree of fulfillment of a rule is given by the membership function, $\mu_i(x_i)$. The fuzzy output of the network will be computed using the centroid rule:

$$z = \sum_{i=1}^{p} \mu_i y_i^* \Big/ \sum_{i=1}^{p} \mu_i.$$

The initial model will be a multiple input single output (MISO) fuzzy inference system with the following IF-THEN rules ($R_i$):

$R_i$: IF $x_1$ is $A_{i1}$ AND $x_2$ is $A_{i2}$ AND . . . AND $x_{30}$ is $A_{i30}$ THEN y is $B_i$ where $i=\overline{1,p}$ and $j=\overline{1,30}$, $A_{ij}$ is the Gaussian membership function of the $i^{th}$ rule associated to the $j^{th}$ input, and $B_i$ is a singleton associated with the output. The output of the initial model will be the weighted average of the outputs of each rule and the multiplication will be used as AND operator.

To obtain a practical and interpretable model, it is desirable to quantify the importance of each input variable. The importance of a given variable can be determined according to the size the output change caused by a specified change to the input variable. Accordingly, a truth value can be assigned to those antecedents associated with a specified input variable in each rule, and a fuzzy inference output can be measured. The range of change of this output is computed, and based on all the ranges computed for each input, an importance factor can be determined for each input. Any input variable with an importance factor smaller than a predefined threshold can be removed as unimportant. Additionally, a correlation function can be computed between the selected input variables. A second threshold can be used to classify the various pairs of input variables as related or not-related according to the computed correlation function. Where a large degree of correlation exists between two variables, the one with a larger importance factor will be retained. The resulting collection of input variables will be selected as inputs for the fuzzy model.

The number of the rules can then be optimized according to a clustering algorithm, as determination of the optimal number of rules is mathematically equivalent to finding a suitable number of clusters for the given data set. In the exemplary implementation, a fuzzy c-means clustering algorithm is used for this purpose. The fuzzy c-means clustering algorithm used for the model attempts to minimize an objective function that incorporates a combination of two measures, compactness within clusters and separation between clusters. The resulting clusters represent the optimal number of rules and a set of initial parameters for the neuro-fuzzy model.

The initial model parameters, specifically the center and standard deviation values of Gaussian membership functions and the weights used in output computation, can be optimized in order to improve performance and accuracy of the model. For example, a back propagation learning algorithm could be utilized with a mean square error (MSE) value calculated as index of performance. Unfortunately, the classic back propagation algorithm can be inefficient or even unable solve a learning problem in some circumstances. Accordingly, a modified back propagation learning algorithm with two parameters, a learning rate parameter and a momentum parameter, can be utilized where the learning rate and the momentum are adjusted through an adaptive algorithm based on changes in performance index.

Additional fuzzy sets can be removed or added according to their relationship with one another in feature space. To this end, similarity measures for the plurality of fuzzy sets can be calculated. Sets having significant overlap in feature space can be merged into a unique single fuzzy set. If the similarity between a fuzzy set and the remaining fuzzy sets is larger than an established threshold, then the fuzzy set can be removed from the antecedent of the appropriate rule. Further, when a membership function of a parameter that expresses a value near zero over the entire expected range of the parameter, the rule associated to the membership function can be removed as the respective rule is not expected to fire. The model can then be further refined according to a parameter fine-tuning mechanism based on a gradient descent algorithm. These refinements allow for a simpler, more interpretable instantiation of the neuro-fuzzy model.

Regardless of the classification system utilized, the results of the classification are provided to a post-processing component 32. The post-processing component can comprise routines for saving and printing the results of the classification and the calculated feature values, as well as routines for automated response to the classification results. For example, the post-processing component can trigger an auditory or visual alarm when a patient's atrial fibrillation index reaches a threshold level. Taken as a whole, the system 10 provides for integrated ECG analysis. The system 10 allows a user to read raw ECG data in MIT format, annotate R-waves, PACs and P-waves, as well as compute PAC activity, HRV and P-wave morphology, and then display, save, and print the analysis results.

Figure 6:
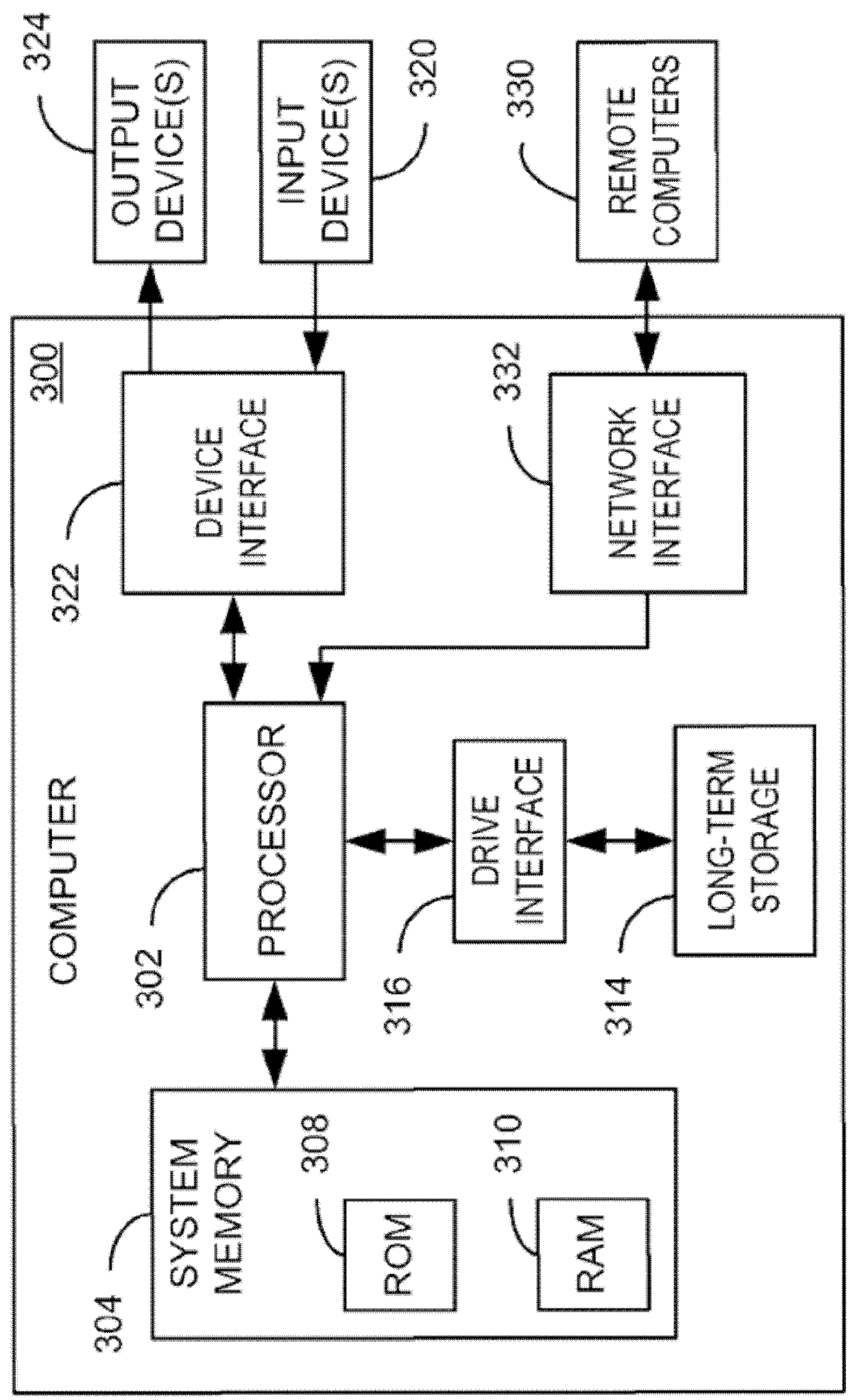
FIG. 6 illustrates a computer system that can be employed to implement systems and methods described herein, such as based on computer executable instructions running on the computer system.

It will be appreciated that the described system for predicting postoperative atrial fibrillation can be implemented, in whole or in part, as a computer program running on a data processing system. FIG. 6 illustrates an exemplary computer system 300 that can be employed to implement systems and methods described herein, such as based on computer executable instructions running on the computer system. The computer system 300 can be implemented on one or more general purpose networked computer systems, embedded computer systems, routers, switches, server devices, client devices, various intermediate devices/nodes and/or stand alone computer systems. Additionally, the computer system 300 can be implemented as part of the computer-aided engineering (CAE) tool running computer executable instructions to perform a method as described herein.

The computer system 300 includes a processor 302 and a system memory 304. Dual microprocessors and other multi-processor architectures can also be utilized as the processor 302. The processor 302 and system memory 304 can be coupled by any of several types of bus structures, including a memory bus or memory controller, a peripheral bus, and a local bus using any of a variety of bus architectures. The system memory 304 includes read only memory (ROM) 308 and random access memory (RAM) 310. A basic input/output system (BIOS) can reside in the ROM 308, generally containing the basic routines that help to transfer information between elements within the computer system 300, such as a reset or power-up.

The computer system 300 can include one or more types of long-term data storage 314, including a hard disk drive, a magnetic disk drive, (e.g., to read from or write to a removable disk), and an optical disk drive, (e.g., for reading a CD-ROM or DVD disk or to read from or write to other optical media). The long-term data storage can be connected to the processor 302 by a drive interface 316. The long-term storage components 314 provide nonvolatile storage of data, data structures, and computer-executable instructions for the computer system 300. A number of program modules may also be stored in one or more of the drives as well as in the RAM 310, including an operating system, one or more application programs, other program modules, and program data.

A user may enter commands and information into the computer system 300 through one or more input devices 320, such as a keyboard or a pointing device (e.g., a mouse). These and other input devices are often connected to the processor 302 through a device interface 322. For example, the input devices can be connected to the system bus 306 by one or more a parallel port, a serial port or a universal serial bus (USB). One or more output device(s) 324, such as a visual display device or printer, can also be connected to the processor 302 via the device interface 322.

The computer system 300 may operate in a networked environment using logical connections (e.g., a local area network (LAN) or wide area network (WAN) to one or more remote computers 330. The remote computer 330 may be a workstation, a computer system, a router, a peer device or other common network node, and typically includes many or all of the elements described relative to the computer system 300. The computer system 300 can communicate with the remote computers 330 via a network interface 332, such as a wired or wireless network interface card or modem. In a networked environment, application programs and program data depicted relative to the computer system 300, or portions thereof, may be stored in memory associated with the remote computers 330.

Figure 7:
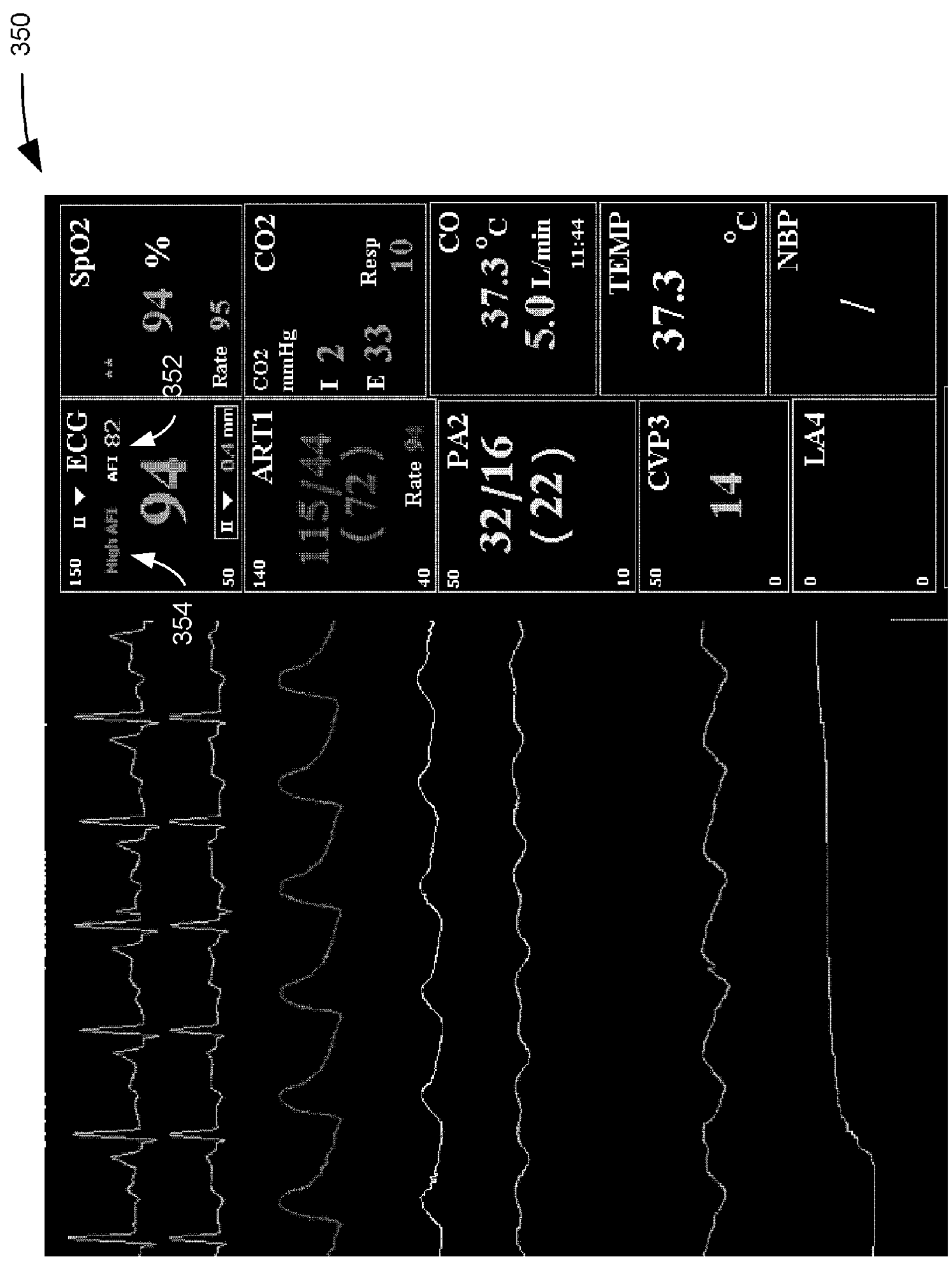
FIG. 7 illustrates a screenshot from an exemplary ECG monitor apparatus for use with an AF prediction system in accordance with an aspect of the present invention.

FIG. 7 illustrates a screenshot 350 from an exemplary ECG monitor apparatus for use with an AF prediction system in accordance with an aspect of the present invention. The AF prediction system can be incorporated into a patient cardiac monitoring apparatus, and the calculated AF index 352 can be displayed on the screen 350 of the monitoring apparatus. It will be appreciated that this screen can be located near the patient, or at a remote location (e.g., a central monitoring station). When the AF index 352 exceeds a threshold value, an alert 354 can be displayed on the monitor to alert the medical staff of the increased risk of artial fibrillation represented by the AF index. At this time steps could be initiated, such as administration of an antiarrhythmic agent, in an attempt to prevent AF. It will be appreciated that this visible alert 354 can be accompanied by an audible alert at the monitor as well as one or more remote locations.

It will be understood that the above description of the present invention is susceptible to various modifications, changes and adaptations, and the same are intended to be comprehended within the meaning and range of equivalents of the appended claims. The presently disclosed embodiments are considered in all respects to be illustrative, and not restrictive. The scope of the invention is indicated by the appended claims, rather than the foregoing description, and all changes that come within the meaning and range of equivalence thereof are intended to be embraced therein.

Having described the invention, the following is claimed:

1. A system for predicting the onset of atrial fibrillation (AF) from an electrocardiogram (ECG) signal representing a patient, comprising:

a signal processing component that determines parameters representing the activity of the heart of the patient from the ECG data, the signal processing component comprising a plurality of R-wave detectors that detect R-waves with respective channels of the ECG signal and a multichannel comparison component that confirms that each R-wave is detected in a threshold number of channels;

a feature extraction component that calculates a plurality of features from the determined parameters, at least one feature being calculated from the detected R-waves; and a classification component that determines an AF index for the patient, representing the likelihood that the patient will experience AF, from the calculated plurality of features.

2. The system of claim 1, each R-wave detector comprising a wavelet-based filter that removes noise and minimizes false identification of R-waves within an associated channel of the ECG signal.

3. The system of claim 1, the classification component comprising a hybrid neuro-fuzzy classification system.

4. The system of claim 1, the feature extractor calculating at least one feature representing premature atrial contraction (PAC) activity.

5. The system of claim 1, the AF index representing an expected time until the onset of atrial fibrillation for the patient.

6. A method for predicting the onset of postoperative atrial fibrillation (AF) from an electrocardiogram (ECG) signal representing a patient, comprising:

determining parameters representing the activity of the heart of the patient from the ECG signal, wherein determining parameters representing the activity of the heart comprises detecting P-waves within the ECG signal by determining a wavelet transform of the ECG signal, selecting a scale for the wavelet transform that contains the maximum P-wave energy, removing irregular beats and arrhythmic segments of the ECG signal, and verifying the presence of two maxima points in a selected segment of the wavelet transformed signal in the selected scale prior to an identified QRS wave to confirm the presence of a P-wave;

extracting a plurality of features from the determined parameters, the plurality of features comprising at least one feature extracted from the detected P-waves within the ECG signal; and determining an AF index for the patient, representing the likelihood that the patient will experience AF, from the calculated plurality of features.

7. The method of claim 6, wherein determining an AF index for the patient comprises providing the extracted plurality of features as inputs to a neural network classifier.

8. The method of claim 6, wherein extracting a plurality of features comprises extracting at least one feature representing heart rate variability in the time domain.

* * * * *